（12) United States Patent
Sugino et al.

(10) Patent No.: US 7,820,613 B2
(45) Date of Patent: Oct. 26, 2010

(54) POWDER SOAP COMPOSITION

(75) Inventors: Masaaki Sugino, Amagasaki (JP);
Kuniaki Tsuruoka, Amagasaki (JP)

(73) Assignee: NOF Corporation, Tokyo (JP)

( * ) Notice: Subject to any disclaimer, the term of this patent is extended or adjusted under 35 U.S.C. 154(b) by 742 days.

(21) Appl. No.: 11/659,584

(22) PCT Filed: Aug. 10, 2005

(86) PCT No.: PCT/JP2005/014974

§ 371 (c)(1),
(2), (4) Date: Feb. 7, 2007

(87) PCT Pub. No.: WO2006/016712

PCT Pub. Date: Feb. 16, 2006

(65) Prior Publication Data

US 2007/0293412 A1    Dec. 20, 2007

(30) Foreign Application Priority Data

Aug. 11, 2004  (JP) .............................. 2004-234269

(51) Int. Cl.
*C11D 17/00* (2006.01)
(52) U.S. Cl. ...................... 510/444; 510/446; 510/452; 510/454
(58) Field of Classification Search .................. 510/446
See application file for complete search history.

(56) References Cited

U.S. PATENT DOCUMENTS

| 2,776,943 | A | | 1/1957 | Eaton |
| 5,298,183 | A | | 3/1994 | Connor et al. |
| 2004/0254088 | A1 | * | 12/2004 | de Ruijter et al. ........... 510/446 |

FOREIGN PATENT DOCUMENTS

| EP | 0057611 A2 | 8/1982 |
| EP | 0460897 A2 | 12/1991 |
| GB | 801018 A | 9/1958 |
| GB | 2027048 A | 2/1980 |
| JP | 51147507 A | 12/1976 |
| JP | 63248899 A | 10/1988 |
| JP | 8003597 A | 1/1996 |
| JP | 10102099 A | 4/1998 |
| JP | 2000160196 A | 6/2000 |
| JP | 2004189621 A | 7/2004 |

* cited by examiner

*Primary Examiner*—Necholus Ogden, Jr.
(74) *Attorney, Agent, or Firm*—The Webb Law Firm

(57) ABSTRACT

A powder soap composition that contains a powder soap made of a fatty acid alkali metal salt. The fatty acid alkali metal salt of the composition contains an alkali metal salt of a saturated fatty acid having 12 to 16 carbon atoms as a main component. The mean particle size of the powder soap is 50 to 500 μm, and the water content of the composition is 3 wt % or less.

7 Claims, No Drawings

POWDER SOAP COMPOSITION

TECHNICAL FIELD

The present invention relates to a powder soap composition. More specifically, the present invention relates to a powder soap composition for the body such as the face and hands.

BACKGROUND ART

Soap is a higher fatty acid alkali metal salt and conventionally has been used in detergents for the body (for the skin) such as the face and hands. As a washing material, soap not only produces a unique fresh feeling after washing but also has good biodegradability and is easy on the environment.

Various such body detergents using the soap have been developed. For example, solid-type, powder-type, liquid-type, and paste-type body detergents have been widely used for years. Of these, powder-type body detergents dissolve more readily than solid-type body detergents, and thus are superior in that they readily dissolve even in cold water and in that only the amount necessary need by discharged, for example. Further, compared to liquid-type and paste-type body detergents, powder-type body detergents are less likely to leak when transported and are less prone to dirty the container when discharged, and thus are easy to use. Consequently, some benefits to powder-type body detergents (soap) are that the sink can be kept clean when they are used, and that they are produced in a form that is highly portable, for example.

Powder soaps normally are produced by preparing an aqueous soap solution, drying the solution by a spray drying method or the like, then adding binder such as water and a non-ionic surfactant, and grinding this into powder with a high-speed mixer, a Henschel mixer, or a Loedige mixer, for example. In order to increasing the solubility, the water content of powder soaps prepared in this manner normally is kept to about 7 to 15%. However, such powder soaps have poor flowability, and blocking readily occurs. Therefore, such powder soaps are preferable only in cases where they are used as clothing detergent that is required high solubility and may be taken out with a measuring cup.

In general, powder-type body detergents are packed into a vessel with a small discharge opening, and when used, it is required to simply discharge a suitable amount of the detergents from the discharge opening. Powder soap that serves as a body detergent therefore is required to have excellent flowability and not be prone to blocking which adversely affects flowability, but to date, a powder soap that has sufficient flowability and anti-blocking property has yet to be obtained.

The fatty acid primarily used as the raw material for soaps is derived from palm oil, coconut oil, and palm kernel, and contains 30 to 40 wt % of unsaturated fatty acid. For example, Japanese Laid-Open Patent Publication No. 8-3597 discloses a powder soap whose main component is sodium oleate, which is an unsaturated fatty acid, and that readily dissolves in cold water. However, although the powder soap obtained by using the unsaturated fatty acid as the raw material has excellent solubility, there is the problem that it may change color or produce foul smells. To solve the problems of changes in color and the production of foul smells, for example, Japanese Laid-Open Patent Publication No. 2000-160196 discloses a soap that uses a saturated fatty acid having 12 to 16 carbon atoms. However, this soap is a solid soap, and when turned into powder, it has poor flowability and blocking occurs. Further, Japanese Laid-Open Patent Publication No. 2004-189621 discloses a powder preparation for face cleansing that contains a sodium saturated fatty acid as a main component and vitamin E and porous silicon dioxide. This powder preparation has good washability and foamability, and leaves an excellent skin feel. Additionally, blocking of the powder preparation is prevented by an addition of large amount of porous silicon dioxide. However, flowability and anti-blocking property of the powder preparation are insufficient. Powder soap that has sufficient flowability and anti-blocking property is desirable.

It is an object of the present invention to provide a powder soap that has good flowability. It is a further object of the present invention to provide a powder soap for the body (for the skin) such as the face and hands that has good solubility, is not prone to blocking, has excellent foamability and foam retention, provides a good feeling of the skin after washing and has excellent storage stability.

SUMMARY OF THE INVENTION

A powder soap composition of the present invention comprises a powder soap made of a fatty acid alkali metal salt; wherein the fatty acid alkali metal salt comprises an alkali metal salt of a saturated fatty acid having 12 to 16 carbon atoms as a main component; wherein the power soap has a mean particle size of 50 to 500 μm; and wherein a water content of the composition is 3 percent by weight (hereinafter, referred to as wt %) or less.

In a preferable embodiment, a fatty acid that constitutes the alkali metal salt of the saturated fatty acid contains 5 to 50 wt % of lauric acid, 40 to 80 wt % of myristic acid, and 5 to 20 wt % of palmitic acid, and the total amount of the lauric acid, the myristic acid, and the palmitic acid is 95 to 100 wt %.

In a preferable embodiment, a sodium content is 50 wt % or more given a total amount of the alkali metal moiety contained in the saturated fatty acid alkali metal salt in the powder soap of 100 wt %.

In a preferable embodiment, the powder soap composition further comprises a saturated fatty acid having 12 to 16 carbon atoms; wherein the saturated fatty acid having 12 to 16 carbon atoms is contained at 1 to 15 parts by weight with respect to 100 parts by weight of the saturated fatty acid alkali metal salt.

In a preferable embodiment, the powder soap has a mean particle size of 50 to 300 μm.

In a preferable embodiment, the powder soap is obtained by the steps comprising: reacting a fatty acid that contains a saturated fatty acid having 12 to 16 carbon atoms as a main component with an alkali metal compound to obtain a soap; obtaining a first drying product by performing a first drying so that the water content of the soap becomes 5 to 15 wt %; and performing a second drying so that the water content of the first drying product becomes 3 wt % or less.

The present invention can achieve the following objectives: providing a powder soap composition whose flowability is good and blocking is not prone to occur; providing a powder soap composition that has good solubility, excellent foamability and foam retention, and provides a good feeling of the skin after washing; providing a powder soap composition that is without the problems of changing color or becoming foul smelling, and that has excellent storage stability, because the composition contains a soap whose main component is a saturated fatty acid alkali metal salt; and providing a powder soap composition that may be used as a powder detergent for body washing that is used for the face and hands.

DETAILED DESCRIPTION OF THE INVENTION

The powder soap composition of the present invention contains a powder soap of a fatty acid alkali metal salt containing an alkali metal salt of a saturated fatty acid having 12 to 16 carbon atoms (a fatty acid alkali metal salt in powder form) as a main component and if necessary, may contain other components. Hereinafter, the powder soap and a composition that contains the powder soap will be described along with the best mode for practicing the invention.

Powder Soap

The powder soap of the present invention contains an alkali metal salt of a saturated fatty acid having 12 to 16 carbon atoms as a main component, and, if necessary, contains other saturated fatty acid alkali metal salts. The powder soap may also contain unsaturated fatty acid alkali metal salts, so long as the problems of changing color or becoming foul smells do not occur.

The alkali metal salt of a saturated fatty acid having 12 to 16 carbon atoms is an alkali metal salt of lauric acid, myristic acid, or palmitic acid. Specific examples thereof include sodium laurate, sodium myristate, sodium palmitate, potassium laurate, potassium myristate, and potassium palmitate.

Examples of other saturated fatty acid alkali metal salts include alkali metal salts of fatty acids such as stearic acid (having 18 carbon atoms), capric acid (having 10 carbon atoms), isostearic acid (having 18 carbon atoms), hydroxystearic acid (having 18 carbon atoms), and behenic acid (having 22 carbon atoms).

The powder soap described above contains an alkali metal salt of a saturated fatty acid having 12 to 16 carbon atoms preferably at least 50 wt %, more preferably at least 70 wt %, and particularly preferably at least 90 wt %. Among the fatty acids that constitute the powder soap (i.e., saturated fatty acid alkali metal salt), it is preferable that fatty acids having 12 to 16 carbon atoms (lauric acid, myristic acid, palmitic acid) are contained at the following concentration. That is, lauric acid is contained in an amount of 5 to 50 wt % and preferably 10 to 40 wt %, myristic acid is contained in an amount of 40 to 80 wt % and preferably 55 to 70 wt %, and palmitic acid is contained in an amount of 5 to 20 wt % and preferably 7 to 15 wt %, and total content of lauric acid, myristic acid, and palmitic acid is 95 to 100 wt %, preferably 97 to 100 wt %. When the content of the lauric acid is less than 5 wt %, the resultant powder soap may have poor foamability, foam retention, and solubility. When the content of the lauric acid is more than 50 wt %, blocking of the resultant powder soap composition may occur and flowability also may worsen. When the content of the myristic acid is less than 40 wt %, foam retention of the resultant powder soap may be decreased, and when the content of the myristic acid is more than 80 wt %, solubility of the resultant powder soap may be decreased. When the content of the palmitic acid is less than 5 wt %, foam retention of the resultant powder soap may be decreased, and when the content of the palmitic acid is more than 20 wt %, the solubility and foamability of the resultant powder soap may be decreased, and the feeling of the skin after washing may become worse. When the total amount of lauric acid, myristic acid, and palmitic acid is less than 95 wt %, the foamability and foam retention of the resultant powder soap may be decreased, and the feeling of the skin after washing may become worse.

Given a total amount of the alkali metal moiety contained in the saturated fatty acid alkali metal salt in the powder soap of 100 wt %, it is preferable a sodium content is 50 wt % or more. Specifically, the alkali metal substantially consists of sodium and potassium. Therefore, it is preferable that the weight ratio of sodium and potassium (i.e., sodium/potassium) is between 100/0 and 50/50 when a total amount of sodium and potassium is 100 parts by weight. In view of increasing the solubility of the powder soap in water, the combination of sodium salts and potassium salts are generally used. Since potassium salts easily become viscous gelatinous substances, potassium salts are generally not used alone. When the weight ratio of sodium/potassium is smaller than 50/50, there may be a drop in the foamability and the foam retention, blocking occurs due to the stickiness, and there also may be a drop in the flowability.

The fatty acid alkali metal salt used in the present invention is obtained by reacting a fatty acid that contains a saturated fatty acid having 12 to 16 carbon atoms as a main component with an alkali metal compound. Examples of the alkali metal compound include sodium hydroxide, potassium hydroxide, sodium carbonate, potassium carbonate or the like. Specifically, an above alkali metal compound is reacted with a fatty acid that contains at least one of lauric acid, myristic acid, and palmitic acid as a main component. There are no particular limitations regarding the reaction conditions, and it is possible to use reaction conditions that are ordinarily used by those skilled in the art to obtain a fatty acid alkali metal salt. The resultant fatty acid metal salt (soap) may be ground up, if necessary, and then subjected to a first drying so that its water content becomes 5 to 15 wt %, and preferably 7 to 13 wt %. The first drying is performed using a drying device that is ordinarily used by those skilled in the art, such as a band dryer for drying soap, a reduced pressure drying tower, or a spray dryer. Then, second drying is performed so that the water content of the first drying product becomes 3 wt % or less, and preferably 1.5 wt % or less. Second drying is performed by using various types of dryers, including kneader-dryers, various vacuum dryers, warm air dryers, and circulation dryers. In this way, a powder soap that has a predetermined water content is obtained. The drying also can be performed after mixing the powder soap and other components as described later.

According to the present invention, by two-step drying as discussed above, the powder soap that has the water content of 3 wt % or less can be obtained. Powder soap with such low water content has good flowability. On the other hand, in general, when manufacturing a powder soap, spray drying is conventionally adopted. By this method, the powder soap having water content of about 7 wt % to 20 wt % is obtained. However, in such an one-step drying method as spray drying, it is difficult to obtain the powder soap that has the water content of less than 7 wt %, and in some cases there also is the risk of dangers such as dust explosion.

In the present invention, the particle size of the powder soap that is obtained by the above process may be suitably adjusted if necessary. For example, to adjust the particle size of the product that is obtained after second drying, grinding, classifying (screening), and the like are performed. When powder soap with a small particle size is obtained, then a high-speed mixer, a Henschel mixer, a Loedige mixer, or various types of classifying devices may be used to carry out granulation or classification.

The powder soap described above has a mean particle size of 50 to 500 μm, preferably 50 to 300 μm, and more preferably 100 to 250 μm. When the mean particle size is less than 50 μm, the powder soap scatters more prevalently and this makes it harder to use, and furthermore, the powder soap may become clumpy when used, which is not preferable. When the mean particle size exceeds 500 μm, the solubility of the resultant powder soap may be decreased and rough deposits form when used.

Powder Soap Composition

The powder soap composition of the present invention, as mentioned above, contains a powder soap made of a fatty acid alkali metal salt, wherein the fatty acid alkali metal salt that contains an alkali metal salt of a saturated fatty acid having 12 to 16 carbon atoms as a main component, and if necessary may contain other components. Examples of other components include fatty acids and various additives.

Among these, fatty acids are added primarily for the purpose of leaving a moist feeling on the skin after washing. As a fatty acid, a saturated fatty acid is preferable, and a saturated fatty acid having 12 to 16 carbon atoms is more preferable.

There are no particular limitations regarding the content of the fatty acid in the powder soap composition. The content of the fatty acid is 1 to 15 parts by weight, preferably 1 to 10 parts by weight, and more preferably 1 to 5 parts by weight with respect to 100 parts by weight alkali metal salts of saturated fatty acids having 12 to 16 carbon atoms. When the amount of the fatty acid, particularly saturated fatty acids having 12 to 16 carbon atoms, is less than 1 part by weight, foam retention of the resultant composition may be decreased, and when the amount of the fatty acid is more than 15 parts by weight, foamability of the resultant composition may be decreased and the composition itself tends to become soft, and therefore the various components in the resultant composition may cause blocking.

The additive contained in the composition normally is a component that those skilled in the art include in detergents, and can be contained in the composition to a degree that does not adversely affect the performance of the present invention. Examples of such additives include powder materials such as silica, talc, activated carbon, kaoline, titanium oxide, sericite, and mica; extracts such as *Ophiopogon* extract, *kippi* extract, *akebia* extract, *peony* root extract, citrus unshiu peel extract, soapberry extract, *Perilla* extract, pecan shell extract, *Polygonum tinctorium* extract, *Portulaca oleracea* extract, coix seed extract, *Areca catechu* extract, Japanese angelica root extract, and grapefruit seed extract; moisturizing agents such as glycerin, polymethacryloyloxyethylphosphorylcholine, squalane, cationic polymer, squalene, hyaluronic acid, and cationic cellulose; various vitamins and their derivates, such as tocopherol, ascorbic acid, and hesperidin; acylglutamic acid salts such as sodium N-lauryl-L-glutamate; surfactants such as acyltaurine salts like N-cocoyl-N-methyl taurine sodium salt; fragrances; pigments; ultraviolet absorbers; fungicides; preservatives; higher alcohols; and esters. If these components are solids, like the powder soap, it is preferable that their mean particle size is 50 to 500 μm.

As mentioned above, the powder soap composition of the present invention contains powder soap and, if necessary, other components (such as fatty acids and various additives). To obtain a powder detergent that contains the various components of this composition, the fatty acids and various additives etc. may be added, if necessary, to the first drying product or the second drying product of the powder soap. As for the fatty acid, the fatty acid remained in the reaction product of the fatty acid alkali metal salt can be used. Such a reaction product of the fatty acid alkali metal salt can be obtained by reacting a fatty acid with an alkali compound in the ratio of a slightly smaller number of moles of the alkali metal compound than the number of moles of the fatty acid.

The mixture that is obtained as the powder soap composition can, if necessary, be further classified and dried, for example.

Although there are no particular limitations regarding the amount of the additive, normally the additive is contained in an amount of 0 to 50 parts by weight with respect to 100 parts by weight alkali metal salt of a saturated fatty acid having 12 to 16 carbon atoms.

Among the above components, it is preferable that those components that are easily damaged by heat, such as the plant extracts, the various vitamins, and the fragrances, are added to the second drying product. For the sake of productivity and costs, it is preferable for the components other than these also to be added to the second drying product.

The mixture (composition) that is ultimately obtained has a water content of 3 wt % or less, preferably 1.5 wt % or less. When the water content exceeds 3 wt %, blocking of the powder soap may occur and flowability of the powder soap may be decreased.

EXAMPLES

Hereinafter, the present invention will be described more specifically by way of examples, but the present invention is not limited to these examples.

The fatty acids, etc., that are used in Examples and the Comparative Examples are the following:

lauric acid: trade name "NAA-122" (produced by NOF CORPORATION)

myristic acid: trade name "NAA-142" (produced by NOF CORPORATION)

palmitic acid: trade name "NAA-160" (produced by NOF CORPORATION)

stearic acid: trade name "NAA-180" (produced by NOF CORPORATION)

28 wt % of sodium hydroxide aqueous solution: prepared by adding distilled water to guaranteed reagent-grade sodium hydroxide 28 wt % of potassium hydroxide aqueous solution: prepared by adding distilled water to guaranteed reagent-grade potassium hydroxide citrus unshiu peel extract: trade name "citrus unshiu peel extract" (produced by NOF CORPORATION)

talc: trade name "rose talc" (produced by Nippon Talc Co., Ltd.)

Example 1

First, approximately 440 g of distilled water was added to fatty acid (45 g of lauric acid, 45 g of myristic acid, and 10 g of palmitic acid), and the resultant fatty acid mixture was stirred at 70° C. Separately, a mixed alkali aqueous solution was prepared by mixing a 28 wt % sodium hydroxide aqueous solution and a 28 wt % potassium hydroxide aqueous solution to a sodium/potassium (Na/K) weight ratio of 85/15. The mixed alkali aqueous solution was added to the above fatty acid mixture while stirring to carry out the reaction. A small quantity of the reaction mixture was removed, and phenolphthalein indicator was added thereto. After the indicator was confirmed to be changed to a slight vermillion color, that shows the point of neutralization, the reaction was immediately stopped.

Next, 1 g each of lauric acid, myristic acid, and palmitic acid was added to the reaction product, and the resultant mixture was dried using a spray drier (GS310; made by Yamato Scientific Co., Ltd.) (first drying). The water content of the first drying product was measured and found to be 10 wt %. The first drying product was further dried (second drying) using a 1-L open kneader (S1-1 type Kneader, made by Moriyama Manufacturing Co., Ltd.). The water content of the second drying product thus obtained was measured and found to be 1.0 wt %. The second drying product that was obtained was ground by Millser (IFM-180G, Iwatani International Corporation), and thus a powder detergent that contains powder soap and fatty acid was obtained. Regarding the powder detergent, mean particle size, angle of repose, and water content were measured. Furthermore, flowability, blocking, foamability, foam retention, solubility, and feeling of the skin after washing were evaluated. These measurements and evaluations were performed according to the following methods. Table 1 shows the results.

<Mean particle size> Mean particle size was measured using the laser diffraction particle size analyzer SALD-2100 (SHIMADZU CORPORATION).

<Angle of repose> The angle of repose was measured using a powder tester (PT-N type) (Hosokawa Micron Corporation).

<Water content> The loss on drying was measured according to JIS-K3304 (105° C., 3 hours).

<Flowability> 50 g of powder detergent was placed in a 100 mL closed vessel with a 5 mm diameter opening and stored for five days under the conditions of 40° C. and 50% humidity. Thereafter, the manner in which the powder flows from the opening was visually evaluated as follows:

open circle: good, powder flows out when the vessel is tipped open triangle: slightly less likely to exit, but flows out when the vessel is shaken X mark: almost no outward flow <Blocking> 50 g of powder detergent was put in a 100 mL closed vessel and stored for five days under the conditions of 40° C. and 50% humidity. Thereafter, when the detergent was transferred to a 1-L beaker, the state of blocking was visually evaluated by the following criteria:

open circle: no blocking at all open triangle: slight blocking

X mark: strong blocking

<Foamability> Ten female panelists in their 10's to 30's took 0.5 g of powder detergent in their hands attempted to produce foam, and scored the foamability based on the following criteria:

2 points: foam created quickly; foamability is good 1 point: although it takes time to produce foam, foamability is good 0 points: very long time before foam is produced; foamability is poor The total score was calculated and evaluated as follows. Table 1 shows the results.

open circle: 14 to 20 points (good foamability)

open triangle: 7 to 13 points (normal foamability)

X mark: 0 to 6 points (poor foamability)

<Foam retention> Ten female panelists in their 10's to 30's took 0.5 g of powder detergent in their hands and produced foam, and scored the foam retention based on the following criteria:

2 points: bubbles do not burst easily, and there is no change in the volume of foam 1 point: bubbles do not burst easily, but with time there is a gradual drop in the volume of foam 0 points: bubbles burst easily, and the volume of foam drops quickly The total score was calculated and evaluated as follows. Table 1 shows the results.

open circle: 14 to 20 points (good foam retention)

open triangle: 7 to 13 points (normal foam retention)

X mark: 0 to 6 points (poor foam retention)

<Solubility> Ten female panelists in their 10's to 30's took 0.5 g of powder detergent in their hands and scored the solubility based on the following criteria:

2 points: dissolves easily, no undissolved detergent remains 1 point: although dissolving takes time, no undissolved detergent remains 0 points: does not dissolve easily, and even after time there is undissolved detergent remaining The total score was calculated and evaluated as follows. Table 1 shows the results.

open circle: 14 to 20 points (good solubility)

open triangle: 7 to 13 points (normal solubility)

X mark: 0 to 6 points (poor solubility)

<Feeling of the skin after washing> Ten female panelists in their 10's to 30's took 0.5 g powder detergent in their hands, dissolved and used the detergent, and scored the feeling of the skin after washing based on the following criteria:

2 points: the detergent provides a good feeling when washed, with no tight or slimy feeling 1 point: the detergent provides a slightly tight and slimy feel 0 points: the detergent provides a strong tight and slimy feel The total score was calculated and evaluated as follows. Table 1 shows the results.

open circle: 14 to 20 points (good skin feel)

open triangle: 7 to 13 points (normal skin feel)

X mark: 0 to 6 points (poor skin feel)

Example 2

First, approximately 440 g of distilled water was added to fatty acid (20 g of lauric acid, 68 g of myristic acid, 10 g of palmitic acid, and 2 g of stearic acid), and the resultant fatty acid mixture was stirred at 70° C. Then, 28 wt % sodium hydroxide aqueous solution (Na/K=100/0) was added to the fatty acid mixture while stirring to carry out the reaction. A small quantity of the reaction mixture was removed, and phenolphthalein indicator was added thereto. After the indicator was confirmed to be changed to a slight vermillion color, that shows the point of neutralization, the reaction was immediately stopped.

Next, 5 g of myristic acid was added to the reaction product, and the resultant mixture was dried using a spray drier (GS310; made by Yamato Scientific Co., Ltd.) (first drying). The water content of the first drying product was measured and found to be 11 wt %. The first drying product was further dried (second drying) using a 1-L open kneader (S1-1 type Kneader, made by Moriyama Manufacturing Co., Ltd.). The water content of the second drying product was measured and found to be 1.2 wt %. The second drying product was ground by Millser (IFM-180G, Iwatani International Corporation), and thus a powder detergent that contains powder soap and fatty acid was obtained. The powder detergent was measured and evaluated in the same manner as in Example 1. Table 1 shows the results.

Example 3

First, approximately 440 g of distilled water was added to fatty acid (30.9 g of lauric acid, 61.8 g of myristic acid, and 10.3 g of palmitic acid), and the resultant fatty acid mixture was stirred at 70° C. Separately, a mixed alkali aqueous solution was prepared by mixing a 28 wt % sodium hydroxide aqueous solution and a 28 wt % potassium hydroxide aqueous solution to a sodium/potassium (Na/K) weight ratio of 70/30.

The mixed alkali aqueous solution was added to the above fatty acid mixture while stirring to carry out the reaction. The amount of adding mixed alkali aqueous solution is such that the amount of alkali metal that is contained is equimolar with the total number of moles calculated from a portion of the fatty acid (30 g of lauric acid, 60 g of myristic acid, and 10 g of palmitic acid) (rate of neutralization 97.0%). Due to the reaction, 3.0% of the fatty acid is present in the free form in the soap.

Next, the reaction product was dried using a spray drier (GS310; made by Yamato Scientific Co., Ltd.) (first drying). The water content of the first drying product was measured and found to be 8 wt %. The first drying product was further dried (second drying) using a 1-L open kneader (S1-1 type Kneader, made by Moriyama Manufacturing Co., Ltd.). The water content of the second drying product was measured and found to be 0.6 wt %. The second drying product that was obtained was ground by Millser (IFM-180G, Iwatani International Corporation), and thus a powder detergent that contains powder soap and fatty acid was obtained. The powder detergent was evaluated in the same manner as in Example 1. Table 1 shows the results.

Example 4

First, approximately 440 g of distilled water was added to fatty acid (30 g of lauric acid, 60 g of myristic acid, 10 g of palmitic acid), and the resultant fatty acid mixture was stirred at 70° C. Separately, a mixed alkali aqueous solution was prepared by mixing a 28 wt % sodium hydroxide aqueous solution and a 28 wt % potassium hydroxide aqueous solution to a sodium/potassium (Na/K) weight ratio of 80/20. The mixed alkali aqueous solution was added to the fatty acid mixture while stirring to carry out the reaction. A small quantity of the reaction mixture was removed, and phenolphthalein indicator was added thereto. After the indicator was confirmed to be changed to a slight vermillion color, that shows the point of neutralization, the reaction was immediately stopped.

Next, 2.5 g of lauric acid was added to the reaction product, and the resultant mixture was dried using a spray drier (GS310; made by Yamato Scientific Co., Ltd.) (first drying). The water content of the first drying product was measured and found to be 9 wt %. The first drying product was further dried (second drying) using a 1-L open kneader (S1-1 type Kneader, made by Moriyama Manufacturing Co., Ltd.). The water content of the second drying product was measured and found to be 0.8 wt %.

65 g of the obtained second drying product, an extract mixture talc obtained by adding 0.1 g citrus unshiu peel extract to 3.4 g talc and uniformly mixing using a mortar, and 31.5 g of talc were mixed uniformly and ground by Millser (IFM-180G, Iwatani International Corporation), and thus a powder detergent was obtained. The powder detergent was evaluated in the same manner as in Example 1. Table 1 shows the results.

Comparative Examples 1 to 4

Powder detergents were obtained using the same manner as in Example 1 using the components listed in Table 1. These powder detergents were evaluated in the same manner as in Example 1. Table 1 shows the results.

TABLE 1

| | | | Example | | | | Comparative Example | | | |
|---|---|---|---|---|---|---|---|---|---|---|
| | | | 1 | 2 | 3 | 4 | 1 | 2 | 3 | 4 |
| Fatty acid alkali metal salt | Composition of fatty acid (Parts by weight) | Lauric acid (C12) | 45 | 20 | 30 | 30 | 45 | 30 | 2 | 30 |
| | | Myristic acid (C14) | 45 | 68 | 60 | 60 | 45 | 60 | 68 | 60 |
| | | Palmitic acid (C16) | 10 | 10 | 10 | 10 | 10 | 10 | 30 | 10 |
| | | Stearic acid (C18) | 0 | 2 | 0 | 0 | 0 | 0 | 0 | 0 |
| | | C12 + C14 + C16*[1] | 100 | 98 | 100 | 100 | 100 | 100 | 100 | 100 |
| | | Sodium/potassium | 85/15 | 100/0 | 70/30 | 80/20 | 85/15 | 70/30 | 100/0 | 90/10 |
| Fatty acid (Parts by weight) | | Lauric acid (C12) | 1.0 | 0 | 0.9 | 2.5 | 2.0 | 0 | 0 | 2.0 |
| | | Myristic acid (C14) | 1.0 | 5.0 | 1.8 | 0 | 0 | 0 | 0 | 0 |
| | | Palmitic acid (C16) | 1.0 | 0 | 0.3 | 0 | 0 | 0 | 0 | 0 |
| | | Stearic acid (C18) | 0 | 0 | 0 | 0 | 0 | 5.0 | 0 | 0 |
| | | Total | 3.0 | 5.0 | 3.0 | 2.5 | 2.0 | 5.0 | 0 | 2.0 |
| Citrus unshiu peel extract (Parts by weight) | | | 0 | 0 | 0 | 0.1 | 0 | 0 | 0 | 0 |
| Talc (Parts by weight) | | | 0 | 0 | 0 | 34.9 | 0 | 0 | 0 | 0 |
| Result | | Mean particle size (μm) | 160 | 172 | 181 | 145 | 612 | 536 | 312 | 600 |
| | | Angle of repose (°) | 0.42 | 0.39 | 0.41 | 0.38 | 0.68 | 0.63 | 0.59 | 0.64 |
| | | Water content (wt %) | 1.0 | 1.2 | 0.6 | 0.8 | 12.1 | 6.0 | 4.3 | 3.1 |
| | | Blocking | ◯ | ◯ | ◯ | ◯ | X | X | Δ | ◯ |
| | | Flowability | ◯ | ◯ | ◯ | ◯ | X | X | Δ | ◯ |
| | | Foamability | ◯ | ◯ | ◯ | ◯ | ◯ | ◯ | X | ◯ |
| | | (Points) | (16) | (18) | (18) | (17) | (16) | (17) | (3) | (15) |
| | | Foam retention | ◯ | ◯ | ◯ | ◯ | ◯ | ◯ | X | ◯ |
| | | (Points) | (17) | (19) | (18) | (18) | (17) | (18) | (2) | (16) |
| | | Solubility | ◯ | ◯ | ◯ | ◯ | X | X | X | X |
| | | (Points) | (18) | (16) | (19) | (19) | (4) | (3) | (3) | (2) |
| | | Feeling of the skin after washing | ◯ | ◯ | ◯ | ◯ | X | X | X | X |
| | | (Points) | (17) | (17) | (18) | (19) | (4) | (5) | (2) | (4) |

*[1]Total amount (parts by weight) of fatty acid having 12 to 16 carbon atoms

The results in Table 1 show that the powder detergents (the powder soap composition of the present invention); which contain a powder soap as a main component, that have water content of 3 wt % or less, and that has mean particle size of 50 to 500 µm; are a small angle of repose, have excellent flowability, occur no blocking. Furthermore, foamability, foam retention, solubility, and feeling of the skin after washing are all good. On the other hand, since the powder detergents of Comparative Examples 1 and 2 have a water content of more than 3 wt % and the large mean particle size, these detergents have a large angle of repose, and poor flowability, and occur blocking. Additionally, the solubility and feeling of the skin after washing of the powder detergents of the Comparative Examples 1 and 2 were also poor. The powder detergent of Comparative Example 3, which satisfies with the mean particle size of the present invention but has higher water content (4.3 wt %), was found to have slightly improved flowability and the blocking, but the foamability, foam retention, solubility, and feeling of the skin after washing of the powder detergent of the Comparative Example 3 were poor. The powder detergent of Comparative Example 4, which has the relatively low water content (3.1 wt %) but has large mean particle size, has poor solubility and feeling of the skin after washing was poor.

The present invention provides a powder soap composition in which the flowability is good, blocking is unlikely to occur, and also the solubility is good, the foamability and foam retention are excellent, and the feeling of the skin after washing is good. Since the powder soap composition contains soap made of a fatty acid alkali metal salt containing an alkali metal salt of a saturated fatty acid having a predetermined number of carbon atoms as a main component, the problem of deterioration as evidenced by color changes and foul smells is obviated and the storage stability is excellent. The powder soap composition of the present invention may be used as a powder soap for body such as the face and hands.

The invention claimed is:

1. A powder soap composition comprising a powder soap made of a fatty acid alkali metal salt,
   wherein the powder soap is obtained by the steps comprising:
   reacting a saturated fatty acid with an alkali metal compound to obtain a soap, wherein the saturated fatty acid comprises 5 to 50 percent by weight of lauric acid, 40 to 80 percent by weight of myristic acid, and 5 to 20 percent by weight of palmitic acid, and the total amount of the lauric acid, the myristic acid and the palmitic acid is 95 to 100 percent by weight; and
   performing a 2-step drying process wherein the water content of the soap after a second drying step is 3 percent by weight or less,
   wherein the powder soap has a mean particle size of 100 to 250 µm; and
   wherein a water content of the composition is 3 percent by weight or less.

2. The powder soap composition of claim 1, wherein a sodium content is 50 percent by weight or more given a total amount of the alkali metal moiety contained in the saturated fatty acid alkali metal salt in the powder soap of 100 percent by weight.

3. The powder soap composition of claim 1, further comprising a saturated fatty acid having 12 to 16 carbon atoms;
   wherein the saturated fatty acid having 12 to 16 carbon atoms is contained at 1 to 15 parts by weight with respect to 100 parts by weight of the saturated fatty acid alkali metal salt.

4. The powder soap composition of claim 1, wherein
   the 2-step drying process comprises: a first drying step wherein the water content of the soap becomes 5 to 15 percent by weight; and
   a second drying step wherein the water content of the soap becomes 3 percent by weight or less.

5. The powder soap composition of claim 2, further comprising a saturated fatty acid having 12 to 16 carbon atoms;
   wherein the saturated fatty acid having 12 to 16 carbon atoms is contained at 1 to 15 parts by weight with respect to 100 parts by weight of the saturated fatty acid alkali metal salt.

6. The powder soap composition of claim 2, wherein
   the 2-step drying process comprises: a first drying step wherein the water content of the soap becomes 5 to 15 percent by weight; and
   a second drying step wherein the water content of the soap becomes 3 percent by weight or less.

7. The powder soap composition of claim 3, wherein
   the 2-step drying comprises process: a first drying step wherein the water content of the soap becomes 5 to 15 percent by weight; and
   a second drying step wherein the water content of the first drying product becomes 3 percent by weight or less.

* * * * *

UNITED STATES PATENT AND TRADEMARK OFFICE
CERTIFICATE OF CORRECTION

| | | |
|---|---|---|
| PATENT NO. | : 7,820,613 B2 | Page 1 of 1 |
| APPLICATION NO. | : 11/659584 | |
| DATED | : October 26, 2010 | |
| INVENTOR(S) | : Sugino et al. | |

It is certified that error appears in the above-identified patent and that said Letters Patent is hereby corrected as shown below:

Column 12, line 40, Claim 7, "drying comprises process" should read
-- drying process comprises --

Signed and Sealed this
Twenty-second Day of February, 2011

David J. Kappos
*Director of the United States Patent and Trademark Office*